(12) United States Patent
Miura et al.

(10) Patent No.: US 7,964,638 B2
(45) Date of Patent: Jun. 21, 2011

(54) SKIN COSMETIC AND WRINKLE-REDUCING AGENT

(75) Inventors: Kyoko Miura, Kanagawa (JP); Akinori Haratake, New York, NY (US)

(73) Assignee: Kao Corporation, Tokyo (JP)

( * ) Notice: Subject to any disclaimer, the term of this patent is extended or adjusted under 35 U.S.C. 154(b) by 604 days.

(21) Appl. No.: 11/918,658

(22) PCT Filed: Apr. 21, 2006

(86) PCT No.: PCT/JP2006/308395
§ 371 (c)(1),
(2), (4) Date: Oct. 17, 2007

(87) PCT Pub. No.: WO2006/115191
PCT Pub. Date: Nov. 2, 2006

(65) Prior Publication Data
US 2008/0293807 A1    Nov. 27, 2008

(30) Foreign Application Priority Data

Apr. 21, 2005  (JP) ................. 2005-124310

(51) Int. Cl.
*A61K 31/31*      (2006.01)
*C07D 493/02*   (2006.01)
*A61P 17/00*      (2006.01)

(52) U.S. Cl. ........................... 514/470; 549/464
(58) Field of Classification Search ............... 514/470; 549/464
See application file for complete search history.

(56) References Cited

U.S. PATENT DOCUMENTS

| 3,272,845 A | 9/1966 | Zech et al. |
| 3,342,680 A | 9/1967 | Treon |
| 4,082,881 A * | 4/1978 | Chen et al. ............... 514/39 |
| 4,169,152 A | 9/1979 | LeMaistre et al. |
| 5,959,066 A * | 9/1999 | Charbonneau et al. ....... 528/271 |
| 6,914,120 B2 * | 7/2005 | Germroth et al. ............ 528/300 |

FOREIGN PATENT DOCUMENTS

| JP | 52-018832 A | 2/1977 |
| JP | 59-025322 A | 2/1984 |
| JP | 61-200921 A | 9/1986 |
| JP | 04217925 A * | 8/1992 |
| WO | WO-01/01949 A1 | 1/2001 |

OTHER PUBLICATIONS

Williams, Adrian, et al, "Penetration Enhancers," Advanced Drug Delivery Reviews, vol. 56, pp. 603-618 (2004).*
S. Hamada et al., "Vitamin A and Derivatives thereof as Anti-wrinkle Material," Fragrance Journal, vol. 26, No. 4, Apr. 15, 1998, pp. 75-77.
"Ismotic," Internet Article, XP002485266, retrieved from the Internet: URL:www.drugs.com/pro/ismotic.html>, retrieved Jun. 17, 2008.
"Isosorbide," Internet Article XP002485265, www.fda.gov/cder/ob, Revtrieved from Internet Jun. 17, 2008.

* cited by examiner

*Primary Examiner* — James D Anderson
*Assistant Examiner* — Zohreh Vakili
(74) *Attorney, Agent, or Firm* — Foley & Lardner LLP

(57) ABSTRACT

The present invention is to provide skin cosmetics and anti-wrinkle agents which are excellent in reducing effect on wrinkle caused by photoaging. Skin cosmetics and anti-wrinkle agents which comprise isosorbide represented by the following formula (1).

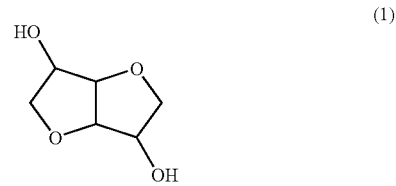

(1)

5 Claims, No Drawings

SKIN COSMETIC AND WRINKLE-REDUCING AGENT

TECHNICAL FIELD

The present invention relates to skin cosmetics and anti-wrinkle agents which have excellent effects of reducing wrinkles occurred due to aging, in particular, at an exposed portion, and have high safety.

BACKGROUND ART

Organs of all the creatures including human grow from birth, and gradually decline with age, then, functions thereof are deactivated. When the deactivated part exceeds a certain extent, the creature dies. The process that the functions thereof are gradually declining is called aging. Skin is directly affected by surroundings and has important functions to maintain circumstance of the inner part of living bodies. Although there is not so much that all of the skin is deactivated, skin is an organ that aging symptoms such as wrinkle, liver spot, dull, slack, etc. are liable to appear thereon, and these symptoms are particularly remarkable at an exposed portion that is exposed to sun light.

When aging of the skin proceeds, protection against stimulus such as oxidative stress, etc. becomes weak, which causes disturbance of internal circumstance of the skin, whereby the skin aging further proceeds. In particular, at the exposed portion, the skin is usually exposed to potent oxidative stress such as UV rays, etc., so that progress of the skin aging is remarkable. Such a change of the skin is referred to as "photoaging". Such a skin leads to undesirable conditions in cosmetic viewpoint that, for example, thickening of epidermis occurs or wrinkles become deep and large at the surface of the skin.

As a substance which has a reducing effect against wrinkles caused by the progress of photoaging, retinoic acid has been used for a prescription drug in the United States. However retinoic acid has potent side effects and involves problems in safety, so that it has not been admitted in Japan (see Non-Patent Literature 1). Accordingly, it has been desired to provide a wrinkle-reducing substance having high safety and sufficient effects.

On the other hand, isosorbide has been utilized in the art of medical products as a substance having high safety, and it has been known, for example, as an osmotic diuretic drug, and applied to a treating agent of Meniere's disease or an oral intraocular pressure-reducing agent, etc. Also, in the art of cosmetics, an ester and an ether of isosorbide have been utilized as a starting material of a nonionic surfactant (Patent Literature 1). However, no investigation has been conducted about a reducing effect of these substances on wrinkles.

Non-Patent Literature 1: Sachio Hamada, Gen Fukuse, "Vitamin A and its derivative as anti-wrinkle material", "FRAGRANCE JOURNAL", published by Fragrance Journal Ltd. on Apr. 15, 1998, vol. 26, No. 4, pp. 75-77

Patent Literature 1: Japanese Patent No. 1147661

DISCLOSURE OF THE INVENTION

Problems to be Solved by the Invention

Thus, an object of the present invention is to provide an anti-wrinkle agent which is excellent in reducing effect on wrinkles which become tangible due to aging, in particular, markedly tangible at the exposed portion, and excellent in effects of maintaining healthy skin from a cosmetic view point.

Means to Solve the Problems

The present inventors have earnestly studied in view of the above-mentioned circumstances, and as a result, they have confirmed that the following anti-wrinkle agent has excellent effects of reducing wrinkles which had been tangible due to aging, in particular, markedly tangible at the exposed portion, and maintaining the skin healthy from a cosmetic viewpoint, and excellent in safety, whereby the present invention has been accomplished.

That is, the present invention is directed to a skin cosmetic which comprises isosorbide represented by the following formula (1).

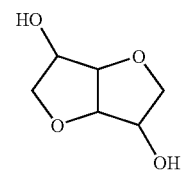

(1)

Also, the present invention is directed to an anti-wrinkle agent which comprises isosorbide represented by the above-mentioned formula (I).

Effects of the Invention

The present invention can provide an anti-wrinkle agent and skin cosmetics, which are excellent in reducing effects on wrinkles occurred due to aging, in particular, at an exposed portion, and can maintain skins in a healthy state in view of skin science and cosmetic points.

BEST MODE TO CARRY OUT THE INVENTION

In the following, embodiments of the present invention are explained in detail.

The isosorbide represented by the following formula (I) to be used in the present invention is commercially available from Tokyo Chemical Industry Co., Ltd., etc.

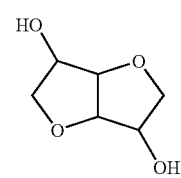

(1)

A formulation amount of the isosorbide in the present invention is preferably 0.001 to 10.0% by mass (hereinafter, simply referred to as "%") based on the total amount of the skin cosmetics or anti-wrinkle agents. It is more preferably 0.01 to 5.0%. If the formulation amount is less than the lower limit, the aimed effects of the present invention are not sufficient, while if it exceeds the upper limit, improvement in effects commensurate with the increased amount cannot be obtained so that it is not preferred.

Incidentally, into the skin cosmetics and anti-wrinkle agents of the present invention, a dye, perfume, antiseptic, surfactant, pigment, anti-oxidant, etc., may be optionally formulated within the range which can accomplish the objects of the present invention, in addition to the above components.

In particular, when ethanol and/or a polyvalent alcohol is/are formulated into the skin cosmetics and anti-wrinkle agents of the present invention, stability of a preparation is maintained and functional characteristics are improved. As the ethanol and/or a polyvalent alcohol to be used in the present invention, there may be mentioned ethanol obtained by known methods such as a fermentation method, etc., or a polyvalent alcohol such as glycerin, diglycerin, polyglycerin, dipropylene glycol, 1,3-butylene glycol, ethylene glycol, diethylene glycol, polyethylene glycol, 1,2-pentanediol, 1,2-hexanediol, 1,2-octanediol, etc. These ethanol and/or a polyvalent alcohol can be formulated in an amount within the range that wrinkle-reducing effects possessed by isosorbide are not impaired, and it is preferably 0.1 to 80.0% based on the total amount of the skin cosmetics or anti-wrinkle agents. It is more preferably 1.0 to 60.0%. If the formulation amount is less than the lower limit or exceeds the upper limit, the effects to be obtained cannot be obtained so that it is not preferred.

EXAMPLES

In the following, the present invention is explained in detail by referring to Examples and Comparative examples.

Wrinkle-reducing effects when a sample comprising a base material alone, or a sample comprising isosorbide had been applied to photoaged skin, were examined according to the following test methods.

1. Experimental Animal 10-weeks old hairless mice at the start of the experiment were used with 10 mice per a group.

2. Measurement of Wrinkle-Reducing Effect 2-1. Photoaging Conditions and Measurement Method Photoaging was induced by irradiating skin with UVA and UVB once a day, five times a week for 8 weeks. An irradiation dose was increased every week from 20 J/cm$^2$, 25 J/cm$^2$ and 30 J/cm$^2$ for UVA, and from 20 mJ/cm$^2$, 30 mJ/cm$^2$ and 40 mJ/cm$^2$ for UVB, and after the 3$^{rd}$ week, the maximum dose was irradiated.

Wrinkle-reducing effects were evaluated by wrinkle score and epidermis thickness. The wrinkle score was graded according to the method of Bissett, et. al. (Photochem Photobiol 46: 367-378, 1987). That is, a size and a depth of the wrinkles were totally evaluated with naked eyes and graded with four-grade. "Large and deep wrinkles can be confirmed" is rated as 3, "wrinkles can be confirmed" as 2, "no wrinkles can be confirmed" as 1, and "normal skin texture can be observed" as 0. Measurement of the epidermis thickness was carried out by collecting whole layer skin, and preparing skin slice specimens according to the conventional manner, and then, applying hematoxylineosin stain thereto, and measuring a thickness of epidermis with an image-analyzing software (Microanalyzer, manufactured by Nihon Poladigital K.K.).

2-2. Samples and Experimental Method

A sample containing 1% of isosorbide in 50% by volume aqueous ethanol solution (a base material) was prepared (Example 1). Also, a sample containing a base material alone was made as Comparative example 1. First, 0.1 mL of each of these samples was applied on the dorsal skin (about 2.5 cm in diameter) of hairless mouse with a frequency of once a day, five times a week, from the 5$^{th}$ week after initiation of UV irradiation to 4$^{th}$ week after completion of the irradiation. After completion of the applying, wrinkle score was graded. After slaughter, skin was collected. The wrinkle score and the epidermis thickness were compared with the base material-applied group as a control.

| (Results of Wrinkle score evaluation) | | |
|---|---|---|
| Group | | Wrinkle score |
| Example 1 | Isosorbide containing sample-applied group | 2.50 ± 0.10 |
| Comparative example 1 | Base material sample-applied group | 2.80 ± 0.20 |

(The values are an average value ± standard error)

Example 1 showed significantly low wrinkle score value as compared with that of Comparative example 1. This indicated that isosorbide is effective to wrinkles induced by photoaging.

| (Results of Epidermis thickness measurement) | | |
|---|---|---|
| Group | | Epidermis thickness (μm) |
| Example 1 | Isosorbide containing sample-applied group | 36.00 ± 3.06 |
| Comparative example 1 | Base material sample-applied group | 43.78 ± 3.13 |

(The values are an average value ± standard error)

In the anti-wrinkle agent-applied group of Example 1, significantly thin epidermis thickness was shown as compared with the applied group of Comparative example 1. This indicated that isosorbide has an effect of reducing the thickening on thickened epidermis due to photoaging. Incidentally, in the case where retinoic acid is applied to this experimental system, it is effective as to wrinkle score. However, with regard to epidermis thickness, retinoic acid acts to enhance thickening, so that this action has been a factor of involving a problem in safety. As compared with this, in isosorbide, there is no such a bad effect and no problem occurred in a normal safety test.

From the results of the present test, it can be understood that the anti-wrinkle agent (Example 1) containing isosorbide clearly has an effect of reducing wrinkles due to photoaging as compared with that of Comparative example 1.

Example 2

In this Example and Comparative example, skin creams having the following composition were prepared according to Preparation method as mentioned below, and used as a sample. Wrinkle-reducing effects were evaluated according to the following operation.

To 5 normal persons (female, 40 to 58-old) who, in questionnaires before the test, mentioned wrinkles at the outer corners of the eyes as a skin problem was applied a skin cream of Example 2 or Comparative example 2. Research on the condition of the skin (wrinkle) at the outer corners of the eyes was carried out by questionnaires according to the manner as mentioned below. Either one of the right or left outer corners of the eyes was decided as a portion to which the sample should be applied, and the other as a comparative portion to which no sample is applied. Each sample was applied on the wrinkle portion of the either one of the right or left outer corners of the eyes (about 4 cm$^2$, 2×2 cm with the outer corner of the eye as a center for each sample), with each about 0.2 mL twice a day, after washing the face in the morning and after bathing in the evening for continuously 2 months (60 days). Next, after completion of the final applying, the members answered questionnaires about the conditions of the skin (wrinkle) at the right and left outer corners of the eyes.

| Composition of skin cream | |
|---|---|
| Components of starting material | Formulation amount (%) |
| Component A | |
| Bees wax | 2.0 |
| Stearic acid | 5.0 |
| Stearyl alcohol | 5.0 |
| Reduced lanorin | 2.0 |
| Squalene | 20.0 |
| Sorbitan monostearate | 3.0 |
| Polyoxyethylene (20) sorbitan monostearate | 3.0 |
| Propylene glycol | 5.0 |
| Component B | |
| Methyl paraben | 0.2 |
| Purified water | Remainder |
| Component C | |
| Isosorbide | 1.0 (Example 2) or 0 (Comparative example 2) |
| Total | 100 |

Preparation Method

Isosorbide which is Component C was added to Component B, and each of Components A and B was dissolved by heating to 80° C., and then mixed. The mixture was cooled to 30° C. under stirring to prepare respective skin creams.

Based on the results of questionnaires, in respective items regarding the condition of skin (wrinkle), the number of persons who answered that the skin cream of Example 2 is more effective than that of Comparative example 2 is shown below.

| Item | Number of person (number) |
|---|---|
| Wrinkle became not conspicuous | 4 |
| Skin became soft | 5 |
| Skin became elastic | 4 |
| Skin became glowing | 4 |
| Skin became light | 3 |

From the results of this test, it can be understood that the skin cream of Example 2 clearly reduces wrinkle as compared with that of Comparative example 2, and that softness or elasticity of skin, which is worsen by photoaging, is also improved. Also, no skin abnormality such as stimulus or itching, etc. due to the skin cream of the present invention was observed.

Example 3

A skin lotion having the following composition was prepared according to a conventional manner, and was used for 2 weeks or longer by 20 normal persons (female, 42 to 58-old) who, in questionnaires before the test, mentioned wrinkles at the outer corners of the eyes as a skin problem. Research was carried out by questionnaires.

| Composition of skin lotion | |
|---|---|
| Components of starting material | Formulation amount (%) |
| Ethanol | 8.0 |
| Polyoxyethylene (60) hydrogenated castor oil | 0.3 |
| Polyoxyethylene (20) sorbitan monolaurate | 0.1 |
| Glycerin | 1.0 |
| Polyethylene glycol 4000 | 0.1 |
| Disodium phosphate | 0.09 |
| Monopotassium phosphate | 0.03 |
| Disodium edetate | 0.02 |
| Methyl paraben | 0.1 |
| Isosorbide | 1.0 |
| Purified water | remainder |
| Total | 100 |

Skin lotion of Example 3 was used by the members and research was carried out by questionnaires. The results are shown below. Incidentally, the results are based on the questionnaires consisted of following items with respect to the conditions of wrinkle, and show the number of persons who answered "yes" with respect to each item comparing the conditions before use and after use.

| Item | Number of person (number) |
|---|---|
| Wrinkle became not conspicuous | 17 |
| Size of wrinkle became small | 17 |
| Number of wrinkles reduced | 6 |
| Number of wrinkles increased | 0 |

From the results of this test, it can be understood that the skin lotion of Example 3 reduces wrinkles due to photoaging. Almost all the members feel that wrinkles became not conspicuous as compared with the condition before use, and as a factor thereof, there are mentioned reduction of a size of wrinkles rather than reduction of the number of wrinkles. Also, no skin abnormality such as stimulus, itching, etc. due to the skin lotion of the present invention was observed.

Example 4

Milky Lotion

A milky lotion of the present invention was prepared with the following composition according to a conventional manner.

| Components of starting material | Formulation amount (%) |
|---|---|
| Hydrogenated lecithin | 1.0 |
| Cholesterol | 0.5 |
| Squalane | 1.0 |
| Octyldodecyl myristate | 3.0 |
| Methylcyclopolysiloxane | 11.0 |
| Dipropylene glycol | 4.0 |
| 1,3-Butylene glycol | 4.0 |
| Glycerin | 7.0 |
| Diglycerin | 2.0 |
| Polyethylene glycol 4000 | 5.0 |
| Methyl paraben | 0.1 |
| Disodium edetate | 0.02 |

-continued

| Components of starting material | Formulation amount (%) |
|---|---|
| Potassium hydroxide | Suitable amount |
| Xanthan gum | 0.01 |
| Alkyl acrylate/methacrylate copolymer | 0.08 |
| Carboxyvinyl polymer | 0.3 |
| Isosorbide | 1.0 |
| Perfume | 0.01 |
| Purified water | remainder |
| Total | 100 |

This milky lotion showed good results in the above-mentioned test.

Example 5

Day Essence

A day essence of the present invention was prepared with the following composition according to a conventional manner.

| Components of starting material | Formulation amount (%) |
|---|---|
| Ethanol | 10.0 |
| Methyl paraben | 0.1 |
| Polyoxyethylene (20) sorbitan monolaurate | 0.4 |
| Polyoxyethylene (60) hydrogenated castor oil | 0.8 |
| Methylcyclopolysiloxane | 2.0 |
| Methylphenylpolysiloxane | 0.5 |
| Squalane | 0.5 |
| Disodium edetate | 0.02 |
| Polyethylene glycol 4000 | 6.0 |
| Glycerin | 10.0 |
| Dipropylene glycol | 4.0 |
| Xanthan gum | 0.04 |
| Carboxyvinyl polymer | 0.3 |
| Isosorbide | 5.0 |
| Perfume | 0.05 |
| Purified water | remainder |
| Total | 100 |

This day essence showed good results in the above-mentioned test.

Example 6

Sun Screen

A sun screen of the present invention was prepared with the following composition according to a conventional manner.

| Components of starting material | Formulation amount (%) |
|---|---|
| Ethanol | 10.0 |
| Octyl methoxycinnamate | 7.0 |
| POE•POP modified dimethylpoylsiloxane | 2.0 |
| Fine particle titanium oxide | 5.0 |
| Zinc oxide | 5.0 |
| Methylcyclopolysiloxane | 20.0 |
| Yolk lecithin | 2.0 |
| Isosorbide | 0.01 |
| Perfume | 0.1 |
| Purified water | Reminder |
| Total | 100 |

This sun screen showed good results in the above-mentioned test.

Incidentally, in Examples, the perfume with the following perfume formulation was used.

| Perfume Formulation A | | | |
|---|---|---|---|
| Component | ‰ by mass | Component | ‰ by mass |
| Terpineol | 10.00 | Vanillin | 2.00 |
| Terpinyl acetate | 2.00 | Ethyl vanillin | 0.10 |
| Cepionate (epi-methyl dihydrojasmonate) | 60.00 | Muscone | 0.50 |
| Methyl dihydro jasmonate | 250.00 | Ethylene brassylate | 42.00 |
| Indol | 0.05 | 4,6,6,7,8,8-Hexamethyl-1,3,4,6,7,8-hexahydrocyclopentabenzopyrane | 60.00 |
| 2-Methyl-3-(3,4-methylene-dioxy-phenyl)-propanal | 3.00 | Cyclopentadecanolide | 20.00 |
| Hydroxy citronellal | 20.00 | Ambrettolide | 1.00 |
| Hydroxy citronellol | 10.00 | γ-Undecalactone | 0.40 |
| p-t-Butyl-α-methylhydro-cinnamic aldehyde | 35.00 | γ-Decalactone | 0.10 |
| 4-(4-Hydroxy-4-methyl-pentyl)-3-cyclohexen-1-carboxyaldehyde | 75.00 | 4-(4-Hydroxypheny)-2-butanone | 0.50 |
| 3-Methyl-5-phenylpentanol | 20.00 | Musk ketone | 0.10 |
| Phenylethyl alcohol | 10.00 | Skatole | 0.01 |
| α-Ionone | 10.00 | cis-Jasmone | 0.05 |
| β-Ionone | 20.00 | Phenyl ethyl acetate | 0.10 |
| γ-methyl ionone | 10.00 | Civetone | 0.20 |
| Dihydro-β-ionone | 25.00 | γ-Nonalactone | 0.05 |
| Benzyl salicylate | 150.00 | α-Santalol | 0.20 |
| cis-3-Hexenyl salicylate | 30.00 | β-Santalol | 0.20 |
| Eugenol | 0.80 | Eugenyl acetate | 0.10 |
| Cinnamic alcohol | 5.00 | α-Hexylcinnamic aldehyde | 20.00 |
| Cinnamic aldehyde | 0.50 | α-Damascone | 0.04 |
| Guaiol acetate | 1.00 | β-Damascone | 0.02 |
| Guaiol | 0.50 | β-Damascenone | 0.01 |
| Cedrenyl acetate | 5.00 | γ-Damascone | 0.01 |
| Methyl cedryl ketone | 30.00 | Rose absolute | 0.50 |
| 6,7-Dihydro-1,1,2,3,3-pentamethyl-4(5H)-indane | 2.00 | Rose oil | 4.50 |
| Vetiver acetate | 10.00 | Sandalwood oil | 2.00 |
| 3-Methyl-5-(2,3,3-trimethyl-3-cyclopenten-1-yl)-pentan-2-ol | 2.00 | Labdanum absolute | 0.05 |
| 2-Ethyl-4-(2,3,3-trimethyl-3-cyclopenten-1-yl)-2-buten-1-ol | 0.80 | Cist absolute | 0.01 |
| Isobornylcyclohexanol | 35.00 | Vetiver oil | 0.50 |
| Heliotropin | 10.00 | Guaiac wood oil | 0.10 |
| Coumarin | 2.00 | Total | 1000.00 |

INDUSTRIAL APPLICABILITY

It can be applied to a skin cosmetic, a medical product and a quasi-drug as an external agent, or a bathing agent, etc. As a preparation form thereof, it can be made, for example, a lotion, a milky lotion, a cream, a pack, etc., and it is extremely useful in view of the beauty of the skin.

The invention claimed is:

1. A method for reducing wrinkles on a skin, comprising applying to wrinkled skin a composition comprising isosorbide of formula (1):

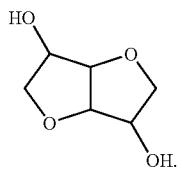

(1)

2. The method of claim 1, wherein the amount of the applied isosorbide ranges from 0.001 to 10.0% by mass based on the total amount of the applied composition.

3. The method of claim 1 or 2, further comprising applying at least one member selected from ethanol and a polyvalent alcohol.

4. The method of claim 3, wherein the polyvalent alcohol is selected from the group consisting of glycerin, diglycerin, polyglycerin, dipropylene glycol, 1,3-butylene glycol, ethylene glycol, diethylene glycol, polyethylene glycol, 1,2-pentanediol, 1,2-hexanediol and 1,2-octanediol.

5. The method of claim 3, wherein the amount of the applied at least one member selected from ethanol and the polyvalent alcohol is 0.1 to 80.0% by mass based on the total amount of the applied composition.

* * * * *